United States Patent [19]
Caruso et al.

[11] Patent Number: 5,985,887
[45] Date of Patent: Nov. 16, 1999

[54] AZA-ANTHRACYCLINONE DERIVATIVES

[75] Inventors: Michele Caruso, Milan; Daniela Faiardi; Tiziano Bandiera, both of Pavia; Jacqueline Lansen; Antonino Suarato, both of Milan, all of Italy

[73] Assignee: Pharmacia & UpJohn S.p.A., Milan, Italy

[21] Appl. No.: 09/000,496

[22] PCT Filed: Jul. 23, 1996

[86] PCT No.: PCT/EP96/03237

§ 371 Date: Feb. 9, 1998

§ 102(e) Date: Feb. 9, 1998

[87] PCT Pub. No.: WO97/06165

PCT Pub. Date: Feb. 20, 1997

[30] Foreign Application Priority Data

Aug. 9, 1995 [GB] United Kingdom ............ 9516349

[51] Int. Cl.$^6$ ............ C07D 211/00; C07D 471/00
[52] U.S. Cl. ............ 514/278; 514/279; 514/281; 546/15; 546/39; 546/44
[58] Field of Search ............ 546/39, 44, 15; 514/279, 281, 278; 536/6.4

[56] References Cited

U.S. PATENT DOCUMENTS

| | | | |
|---|---|---|---|
| 5,637,572 | 6/1997 | Merlini et al. | 514/34 |
| 5,731,313 | 3/1998 | Suarato et al. | 514/255 |
| 5,744,454 | 4/1998 | Suarato et al. | 514/34 |

OTHER PUBLICATIONS

J. Med. Chem., vol. 31(2), pp. 433–444, Grunewald, 1988.

*Primary Examiner*—D. Margaret M. Mach
*Attorney, Agent, or Firm*—Oblon, Spivak, McClelland, Maier & Neustadt, P.C.

[57] ABSTRACT

Compounds of formula I

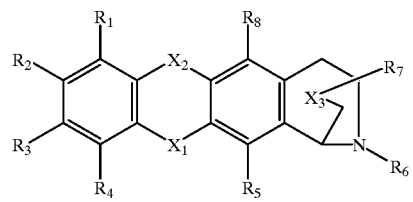

wherein $X_1$ and $X_2$ are C=O, C=NH or $CH_2$, $X_3$ is $CH_2$, CO, CHOH,

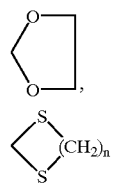

wherein n=2 or, 3 or C=N($R_9$) wherein $R_9$ is hydroxy or amino-aryl, and each of $R_1$, $R_2$, $R_3$, $R_4$, $R_5$, $R_6$, $R_7$ and $R_8$ are hydrogen, halogen or an organic residue, are useful in the treatment of amyloidosis. A process for their preparation and pharmaceutical compositions containing them are also described.

13 Claims, No Drawings

AZA-ANTHRACYCLINONE DERIVATIVES

This application is a 371 of PCT/EP96/03237, filed Jul. 23, 1996. Priority is based upon application no. GB 9516349.9, having a filing date of Aug. 9, 1995, which application is incorporated herein by reference in the entirety.

BACKGROUND OF THE INVENTION

1. Field of the Invention

The present invention relates to novel aza-anthracyclinone derivatives, their use for the treatment of amyloidosis, methods for their preparation and pharmaceutical compositions containing them.

2. Description of the Background

The relationship between amyloidosis, cell death and loss of tissue function appears to be of relevance for different type of disorders including neurodegenerative disorders. Therefore, the prevention of amyloid formation and/or the induction of amyloid degradation can be an important therapeutic tool for all pathological disorders associated with amyloidosis including AL amyloidosis and neurodegenerative disorders of the Alzheimer's type.

SUMMARY OF THE INVENTION

The present invention provides novel aza-anthracyclinones and their use in the treatment of amyloidosis. The new compounds are characterized by the presence of a bridged heterocyclic ring fused with an anthraquinone system.

The new class of molecules is named anthrazalinone and the parent compound, indicated as anthrazalone, may be considered related to the 8-aza-anthracyclinones

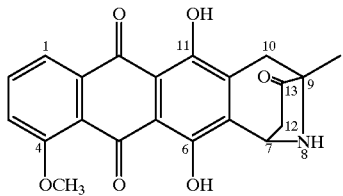

Anthrazalone

DETAILED DESCRIPTION OF THE INVENTION

More particularly, the present invention provides an anthrazalinone derivative of formula 1

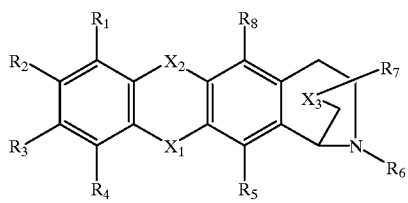

1 wherein:
$X_1$ and $X_2$ are independently selected from;
C=O,
C=NH, and
$CH_2$, $X_3$ is selected from
$CH_2$,
C=O,
CHOH,

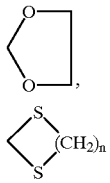

wherein n=2 or 3, and
C=N($R_9$) wherein $R_9$ is hydroxy or amino-aryl,
$R_1$, $R_2$, $R_3$ and $R_4$ are independently selected from hydrogen,
hydroxyl,
$C_{1-16}$ alkyl,
$C_{1-16}$ alkoxyl,
$C_{3-8}$ cycloalkoxyl,
halogen,
amino which may be unsubstituted or mono- or di-substituted by acyl, trifluoroacyl, aralkyl or aryl groups and
$OSO_2$ ($R_{10}$) wherein $R_{10}$ is alkyl or aryl;
$R_5$ and $R_8$ are independently selected from
hydrogen,
hydroxyl,
$C_{1-16}$ alkoxyl,
halogen,
amino which may be unsubstitued or mono- or di-substituted by acyl, trifluoroacyl, aralkyl or aryl groups, and
$OSO_2$ ($R_{10}$) wherein $R_{10}$ is as above defined;
$R_6$ is selected from
hydrogen,
$R_B$—$CH_2$— wherein $R_B$ represents an aryl or heterocyclyl group or a group of formula $R_C$—CH=CH—, wherein $R_C$ is hydrogen or $C_{1-5}$ alkyl,
$C_{1-16}$ alkyl,
$C_{2-8}$ alkenyl,
$C_{3-8}$ cycloalkyl,
acyl of formula —C($R_{11}$)=O wherein $R_{11}$ is selected from hydrogen,
$C_{1-16}$ alkyl,
$C_{3-8}$ cycloalkyl,
hydroxyalkyl, heterocyclyl, aryl
araloxyalkyl,
acyloxyalkyl and
a residue of a naturally occurring amino acid, for example glycine, cysteine, phenylalanine or leucine or a synthetic amino acid or a residue of a di- or tri-peptide, for example Gly-Gly, Gly-Phe, Gly-Leu, or Gly-Phe-Leu, Gly-Leu-Phe; and
$R_7$ is selected from
hydrogen,
methyl,
$CH_2OH$,
$CH_2O$—$R_{12}$ wherein $R_{12}$ is the group tetrahydropyranyl (THP), or a saccharide of the formula

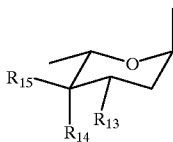

in which $R_{13}$ is amino or aminoacyl, $R_{14}$ and $R_{15}$ are both hydrogen or one of $R_{14}$ or $R_{15}$ is hydrogen and the other of $R_{14}$ or $R_{15}$ is hydroxy or alkoxy or halogen or a group $OSO_2$ ($R_{10}$) as previously defined, $CH_2$—O—Ph—(amino) wherein the amino may be unsubstitued or mono- or di-substituted by an alkyl, acyl, trifluoroacyl, aralkyl or aryl group; and $CH_2$-amino wherein the amino is mono- or di-substituted by an alkyl, acyl, trifluoroacyl, aralkyl or aryl group or the amino is within an heterocyclic ring, for example a piperidino, pyrrolidino or morpholino ring optionally substituted with $C_{1-16}$ alkyl or $C_{1-16}$ alkyloxy or aryloxy, or a pharmaceutically acceptable salt thereof. Preferred compounds of formula 1 are those wherein:

$X_1$ and $X_2$ are independently selected from
  C=O and
  C=NH;
$X_3$ is selected from
  $CH_2$,
  C=O,
  CHOH and
  C=N($R_9$) wherein $R_9$ is hydroxy or amino-aryl,
$R_1$, $R_2$, $R_3$ and $R_4$ are independently selected from
  hydrogen,
  hydroxyl,
  $C_{1-4}$ alkoxyl,
  $C_{3-8}$ cycloalkoxyl,
  O-mesyl (O—$SO_2CH_3$),
  amino and
  amino-benzyl;
$R_5$ and $R_8$ are independently selected from
  hydrogen,
  hydroxyl,
  $C_{1-4}$ alkoxyl,
  halogen,
  amino,
  amino-benzyl and
  amino-trifluoroacetyl;
$R_6$ is selected from
  hydrogen,
  $R_B$—$CH_2$, wherein $R_B$ is as defined above,
  $C_{1-10}$ alkyl,
  $C_{2-6}$ alkenyl,
  acyl of formula —C($R_{12}$)=O wherein $R_{12}$ is selected from
  $C_{1-10}$ alkyl,
  hydroxyalkyl, heterocyclyl, aryl
  araloxyalkyl,
  acyloxyalkyl and
  a residue of a naturally occurring amino acid, for example glycine, cysteine, phenylalanine, leucine, or a synthetic amino acid or a residue of a di- or tri-peptide for example Gly-Gly, Gly-Phe, Gly-Leu, Gly-Phe-Leu, Gly-Leu-Phe; and
$R_7$ is selected from
  hydrogen,
  methyl,
  $CH_2OH$,
  $CH_2O$—$R_{12}$ wherein $R_{12}$ is the group tetrahydropyranyl (THP), or a saccharide of the formula

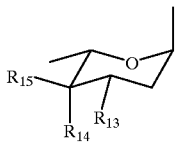

in which $R_{13}$ is amino or aminotrifluoroacetyl or aminoacetyl, $R_{15}$ is hydrogen and $R_{14}$ is hydroxy or iodine or O-mesyl, $CH_2$—O—Ph—NH—COR wherein R is alkyl, aralkyl or aryl, $CH_2$-amino wherein the amino is within an heterocyclic ring for example a piperidino, pyrrolidino, morpholino or dihydropyridino ring optionally substituted with $C_{1-10}$ alkyl or $C_{1-5}$ alkyloxy or aryloxy.

More preferred compounds of formula 1 are those wherein:

$X_1$ and $X_2$ are independently selected from
  C=O and
  C=NH;
$X_3$ is selected from
  $CH_2$,
  C=O and
  CHOH,
$R_1$, $R_2$, $R_3$ and $R_4$ are independently selected from
  hydrogen,
  hydroxyl,
  methyl,
  methoxy,
  O-mesylate,
  amino,
  amino-benzyl,
  fluorine and
  chlorine;
$R_5$ and $R_8$ are independently selected from
  hydrogen,
  hydroxyl,
  methoxy,
  ethoxy,
  amino and
  amino-trifluoroacetyl;
$R_6$ is selected from
  hydrogen,
  benzyl,
  allyl,
  3,4-dimethoxybenzyl,
  pyridinmethyl,
  (N-methyl-dihydropyridine)-methyl,
  nicotyl,
  glycyl and
  isoleucyl; and
$R_7$ is selected from
  hydrogen,
  methyl,
  $CH_2OH$,
  $CH_2O$—$R_{12}$ wherein $R_{12}$ is the group tetrahydropyranyl (THP), or a saccharide of the formula

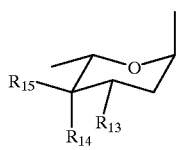

in which $R_{13}$ is amino or aminotrifluoroacetyl or aminoacetyl, $R_{15}$ is hydrogen and $R_{14}$ is iodine and $CH_2$-amino wherein the amino is within a morpholino ring.

Further preferred compounds of the formula 1 are those wherein:

$X_1$ and $X_2$ are both C=O;

$X_3$ is C=O;

$R_1$, $R_2$ and $R_3$ are each hydrogen and $R_4$ is hydrogen, hydroxy or methoxy;

$R_5$ and $R_8$ are independently selected from hydrogen, hydroxyl, methoxy and amino;

$R_6$ is selected from hydrogen, pyridinmethyl, (N-methyldihydropyridine)-methyl, nicotyl, glycyl and isoleucyl; and $R_7$ is methyl.

An "alkyl" group is typically a $C_1$–$C_{16}$ alkyl group. A $C_1$–$C_{16}$ alkyl group includes both straight and branched chain alkyl groups. Preferably a $C_1$–$C_{16}$ alkyl group is a $C_1$–$C_{12}$ alkyl group such as hexyl, isohexyl, heptyl, octyl, nonyl, decyl, undecyl and dodecyl groups or a branched chain isomer thereof. Preferably, a $C_1$–$C_{12}$ alkyl group is a $C_1$–$C_6$ alkyl group or a $C_1$–$C_5$ alkyl group such as a methyl, ethyl, propyl, isopropyl, butyl, t-butyl, isobutyl or pentyl group, or a branched chain isomer thereof. The alkyl groups discussed above may be substituted with one or more substituents, for example a halo substituent such as fluorine, chlorine, bromine or iodine, $CF_3$, an alkoxy substituent, an aryl substituent, an alkyl-aryl substituent, a haloaryl substituent, a cycloalkyl substituent or an alkylcycloalkyl substituent.

The term "alkenyl" as used herein includes both straight and branched chain radicals of up to 8 carbons, or example allyl, butenyl, hexenyl, octenyl.

The term "cycloalkyl" as used herein means a cycloalkyl group having 3 to 8 carbons, preferably from 3 to 5 carbons. Examples include cyclopropyl, cyclopentyl, cyclopentylmethyl, cycloheptyl and cyclooctyl.

The heterocyclyl group is a 3- to 6-membered, for example a 3, 4, 5 or 6-membered, saturated or unsaturated heterocyclyl ring containing at least one heteroatom selected from O, S and N, which is optionally fused to a second 5- to 6-membered, saturated or unsaturated heterocyclyl group or to a said cycloalkyl group or to an aryl group as defined hereinbelow. Examples of heterocyclyl groups are pyrrolyl, imidazolyl, triazolyl, tetrazolyl, oxazolyl, thiazolyl, thiadiazolyl, thienyl, piridinyl, dihydropyridinyl, piperidinyl, piperazinyl, pyrazinyl, pirimidinyl, pyranyl, pyridazinyl, furanyl, pyrazolyl, isothiazolyl, isoxazolyl, morpholinyl, thiopyranyl, benzothienyl, benzothiazolyl or benzoxazolyl group.

Such groups may be substituted with hydroxy, primary or secondary amino, or tertiary amino groups, the radicals on the secondary and tertiary amino being, for instance, $C_1$–$C_{12}$ straight or branched alkyl groups, phenyl, benzyl, alkoxy, phenoxy or benzyloxy groups or halogen atoms.

The term "aryl" as employed herein includes both monocyclic or bicyclic aromatic groups containing from 6 to 10 carbons in the ring portion, such as phenyl, naphthyl, substituted phenyl or substituted naphthyl, wherein the substituent on either the phenyl or naphthyl may be for example $C_{1-6}$ alkyl, halogen or $C_{1-6}$ alkoxy.

The term "halogen" as used herein means fluorine, chlorine, bromine or iodine.

The term "aralkyl" as used herein refers to alkyl groups as previously discussed having an aryl substituent, as defined above, for example benzyl; 3,4 dimethoxybenzyl, phenethyl, diphenylmethyl and triphenylmethyl.

The term "aroyl" as used herein refers to a group of the formula —COAr wherein Ar denotes an "aryl" group as defined above.

The term "alkoxy" or "aryloxy" as used herein includes any of the above alkyl or aralkyl groups linked to an oxygen atom. The term "alkoxyalkyl" as used herein means any alkyl as discussed above linked to any alkoxy as discussed above, for example ethoxypropyl.

The term "aryloxyalkyl" as used herein means any alkyl as discussed above linked to an aryl as discussed above by an oxygen atom, for example phenoxyethyl.

The term "araloxyalkyl" as used herein means an aralkyl as discussed above linked to an alkyl as discussed above by an oxygen atom, for example benzyloxyethyl.

The term "acyloxyalkyl" as used herein means an $C_1$–$C_{10}$ acyl group inked to an alkyl group as defined above by an oxygen atom, for example acetoxymethyl.

The term "hydroxyalkyl" as used herein means an alkyl group as discussed above bounded to a hydroxyl group, for example hydroxyethyl. An acyl group is typically a $C_1$–$C_{10}$ acyl group, for example a $C_1$–$C_6$ acyl group such as a methanoyl, ethanoyl, n-propanoyl, i-propanoyl, n-butanoyl, t-butanoyl, sec-butanoyl, pentanoyl or hexanoyl group.

This invention also includes all the possible isomers of compounds of the formula (I) and mixtures thereof, for example diastereoisomeric mixtures and racemic mixtures. Thus, the stereocentres at the 7-position and the 9-position may be in the R or the S configuration (or both i.e. a mixture of stereoisomers is present). Similarly, the glycosidic linkage of the saccharide may be in the α or β configuration (or both, i.e. a mixture of stereoisomers is present). The present invention also provides the salts of those compounds of formula 1 that have salt-forming groups, especially the salts of the compounds having a carboxylic group or a basic group (e.g. an amino group).

The present invention includes salts of the anthrazalinone derivative of the formula 1. The salts are typically physiologically tolerable or pharmaceutically acceptable salts, for example alkali metal and alkaline earth metal salts (e.g. sodium, potassium, lithium, calcium and magnesium salts), ammonium salts and salts with an appropriate organic amine or amino acid (e.g. arginine, procaine salts), and the addition salts formed with suitable organic or inorganic acids, for example hydrochloric acid, sulfuric acid, carboxylic acid and sulfonic organic acids (e.g. acetic, trifluoroacetic, p-toluensulphonic acid).

Compounds of formula 1 wherein $R_6$ represents a $R_B$-$CH_2$ group can be prepared by: (a) reacting a compound of formula 2

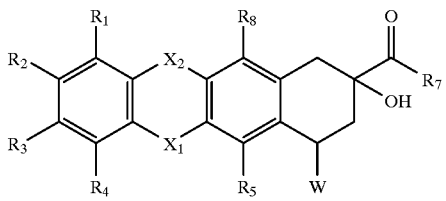

wherein $X_1$, $X_2$ and $R_1$ to $R_7$ are as defined above, and W represents a leaving group, with an amine of the formula

wherein $R_B$ is as defined above, to give a compound of formula I wherein $R_6$ is $R_B$—$CH_2$—;

(b) if desired, converting the thus obtained compound of formula (I) into another compound of formula (I); and/or
(c) if desired, converting the compound of formula (I) to a pharmaceutically acceptable salt thereof.

Suitable groups W include O-saccharide such as O-daunosaminyl derivatives, O-acyl such as example O-trifluoro-acetyl or O-(p-nitrobenzoyl) or O-ethoxycarbonyl, O-acetal such as O-THP. Preferred amines of formula $NH_2$—$CH_2$—$R_B$ include alkylaryl amines, for example benzylamine, 3,4-dimethoxybenzyl amine or pyridinmethylamine.

A compound of formula 2 is typically reacted with an amine of formula $H_2N$—$CH_2R_B$ as above defined. The amine is typically present at from 1 to 10 fold excess. The reaction may take place in a compatible organic solvent such as methylene chloride or pyridine. An organic base, such as pyridine, may be present. The reaction may take place for a period of 6 to 48 hours, typically from $-10°$ C. to room temperature (i.e. about $20°$ C.).

Preferably a four fold excess of amine of formula $H_2N$—$CH_2R_B$ is used. The solvent is most typically pyridine. Preferred reaction conditions are room temperature for a period of from 12 to 24 hours.

It should be stressed that this reaction is new in the field of the chemistry of anthracyclines and anthracyclinones. Anthrazalinone derivatives in which $R_6$ represents hydrogen, may be prepared, for example, by deblocking the corresponding N—$CH_2R'_B$ derivative wherein $R'_B$ is a 3,4 dimethoxyphenyl or vinyl group. The de-blocking is typically achieved by oxidation, for example by treatment with 5,6-dicyano-1,4-benzoquinone (DQQ). The reaction may be conducted in the presence of a suitable solvent. Preferably an equivalent amount of DDQ is used. Preferably, the solvent is a mixture of methylene chloride and water (typically in a ratio 20:1 by volume). The reaction is typically conducted at room temperature for from 1 to 6 hours.

Anthrazalinone derivatives of formula 1 may be further functionalized to different 8-N-substituted derivatives by means of standard chemical procedures.

For example 8-N-alkyl, -alkenyl, -cycloalkyl anthrazalinones of formula 1 are preferably prepared by reacting a compound of formula 1 in which $R_6$ is hydrogen with a group of formula $R_6$-X wherein $R_6$ is $C_1$–$C_{16}$ alkyl, $C_2$–$C_8$ alkenyl or $C_3$–$C_8$ cycloalkyl and X is a leaving group such as a halogen, O—$SO_2CH_3$, O—$SO_2CF_3$ or O—$SO_2$—$C_6H_4CH_3$. Preferably X is halogen. More preferably, X is iodine. A suitable solvent may be present. A 2 to 20 fold excess of $R_6$-X is preferably used. Preferably, the reaction is conducted in an organic solvent such as methylene chloride or dimethylformamide. The reaction typically takes place at from 40 to $80°$ C. for from 4 to 24 hours.

8-N-acyl-anthrazalinones of formula 1 are preferably prepared by reacting a compound of formula 1 in which $R_6$ is hydrogen with an acyl derivative of formula $R_{11}$—CO—Hal or $(R_{11}CO)_2O$ wherein $R_{11}$ is as above defined and Hal is halogen, preferably chlorine. A 2 to 20 fold excess of acyl derivative is preferably used. A solvent is typically present, for instance an organic solvent such as methylene chloride or dimethylformamide. Preferably the reaction is conducted at from $-10$ to $40°$ C. for from 1 to 24 hours.

In a further example, N-acyl-anthrazalinones of formula 1 may be prepared by reacting an anthrazalinone of formula 1 in which $R_6$ is hydrogen with an acid derivative of formula $R_{11}$—COOH in presence of a condensing agent such as dicyclohexylcarbodiimide or 2-ethoxy-1-ethoxycarbonyl-1, 2-dihydroquinone (EEDQ) in an anhydrous organic solvent. A 1 to 4 fold excess of acid is preferred. Preferably the dry organic solvent is dimethylformamide. An equivalent amount of EEDQ is typically used. The reaction is generally conducted at room temperature for 15 hours.

The compounds of the formula I, wherein $R_6$ is a residue of an amino acid or a di- tripeptide may be analogously prepared according to the condensation conditions known in peptide chemistry.

Also the C-13-carbonyl group may be reduced to C-13-dihydro or functionalized to hydrazone and then reduced to afford C-13-deoxo derivatives by means of procedures already known from the chemistry of the anthracyclines.

For example, in order to prepare C-13-dihydro derivatives of formula 1, an anthrazalinone of formula 1 ($X_3$=CO) is reacted with a reducing agent in an organic solvent at from $-10°$ C. to room temperature for from 5 to 30 minutes.

Preferred conditions encompass dissolving an aglycone of formula 1 as previously defined in dry methylene chloride and treating it with 5 to 10 fold excess of tetrabutylamonium borohydride at room temperature for 5 minutes.

Compounds of formula 2 are available from natural sources or may be prepared by following by known synthetic methods starting from known anthracyclines or anthracyclinones. For example, 7-O-saccharide in which the sugar is daunosaminyl may be derived from a natural source such as daunorubicin, or may be prepared by means of synthetic modification of the same.

Other aglycones functionalised at position C-7 may be prepared by means of well known procedures.

For example, 7-O-THP derivatives of formula 2 (compounds wherein W is 0-THP) are easily prepared by reacting an aglycone of formula 3:

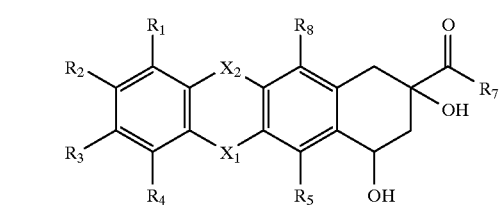

with dihydropyrane in an organic solvent and in the presence of an acid catalyst at room temperature for 1 to 4 hours. Preferably the compound of formula 3 is dissolved in methylene chloride and reacted with 4 equivalents of dihydropyrane in the presence of a catalytic amount of p-toluensulfonic acid at room temperature for 2 hours. The 7-O-TPH derivative is recovered by washing the reaction mixture with aqueous sodium hydrogen carbonate and water, then removing the solvent under reduced pressure.

7-O-acyl derivatives of formula 2 are prepared by reacting the compound of formula 3 with a suitable carboxylic acid, acid anhydride or acyl chloride in organic solvent and in the presence of a base at from −10 to room temperature for from 1 to 6 hours.

For example a 7-O-acetyl derivative of formula 2 (W=O—COCH$_3$) is prepared by reacting the compound of formula 3 with acetic anhydride in an organic solvent such as methylene chloride and in the presence of an organic base such as pyridine.

The compound is recovered by precipitating the crude material in apolar solvent such as hexane.

Some of the starting materials for the preparation of compounds of formula 1 are known, the others may be analogously prepared starting from known anthracyclines or anthracyclinones by means of known procedures.

For example, the following anthracyclines are known and can be represented by the same formula 2:

daunorubicin (2a: $R_1=R_2=R_3=H$, $R_4=OCH_3$, $R_5=R_8=OH$, $X_1=X_2=CO$, $R_7=CH_3$, $L=O$-daunosaminyl), doxorubicin (2b: $R_1=R_2=R_3=H$, $R_4=OCH_3$, $R_5=R_8=OH$, $X_1=X_2=CO$, $R_7=CH_2OH$, $L=O$-daunosaminyl), 4-demethoxydaunorubicin (2c: $R_1=R_2=R_3=R_4=H$, $R_5=R_8=OH$, $X_1=X_2=CO$, $R_7=CH_3$, $L=O$-daunosaminyl), 11-desoxydaunorubicin (2d: $R_1=R_2=R_3=H$, $R_4=OCH_3$, $R_5=OH$, $R_8=H$, $X_1=X_2=CO$, $R_7=CH_3$, $L=O$-daunosaminyl), 11-aminodaunorubicin (2e: $R_1=R_2=R_3=H$, $R_4=OCH_3$, $R_5=OH$, $R_8=NH_2$, $X_1=X_2=CO$, $R_7=CH_3$, $L=O$-daunosaminyl), 6-deoxydaunorubicin (2f: $R_1=R_2=R_3=H$, $R_4=OCH_3$, $R_5=H$, $R_8=OH$, $X_1=X_2=CO$, $R_7=CH_3$, $L=O$-daunosaminyl), 6-aminodaunorubicin (2g: $R_1=R_2=R_3=H$, $R_4=OCH_3$, $R_5=OH$, $R_8=NH_2$, $X_1=X_2=CO$, $R_7=CH_3$, $L=O$-daunosaminyl), 4-aminodaunorubicin (2h: $R_1=R_2=R_3=H$, $R_4=NH_2$, $R_5=R_8=OH$, $X_1=X_2=CO$, $R_7=CH_3$, $L=O$-daunosaminyl), 9-deacetyl-9-formyl-N-trifluoroacetyldaunorubicin (2i: $R_1=R_2=R_3=H$, $R_4=OCH_3$, $R_5=R_8=OH$, $X_1=X_2=CO$, $R_7=H$, $L=O$-(N-trifluoroacetyl-daunosaminyl).

Also some 7-O-derivatives of formula 2 are known, for example 7-O-ethoxycarbonyldaunomycinone (2j: $R_1=R_2=R_3=H$, $R_4=OCH_3$, $R_5=R_8=OH$, $X_1=X_2=CO$, $R_7=CH_3$, $L=O—COOC_2H_5$), 7-O-(tetrahydropyranyl)-daunomycinone (2k: $R_1=R_2=R_3=H$, $R_4=OCH_3$, $R_5=R_8=OH$, $X_1=X_2=CO$, $R_7=CH_3$, $L=O$-THP), 7-O-acetyldaunomycinone (2l: $R_1=R_2=R_3=H$, $R_4=OCH_3$, $R_5=R_8=OH$, $X_1=X_2=CO$, $R_7=CH_3$, $L=O—COCH_3$).

The compounds of the present invention are characterized by high inhibitory activity on amyloidosis. The present invention therefore further provides the use of a compound of formula I, as above defined, or a pharmaceutically acceptable salt thereof, in the treatment of amyloidosis.

A human or animal, e.g. a mammal, may thus be treated by a method which comprises the administration thereto of a compound of formula (I) or a pharmaceutically acceptable salt thereof. The term amyloidosis indicates various diseases whose common characteristic is the tendency of particular proteins to aggregate and precipitate, as insoluble fibrils, into the extracellular space causing structural and functional damage to organ and tissues. The classification of amyloid and amyloidosis has been recently revised in Bulletin of the World Health Organisation 71(1): 105 (1993).

All the different types of amyloid share the same ultrastructural organization in anti-parallel β-pleated sheets despite the fact that they contain a variety of widely differing protein subunits [see: Glenner G. G., New England J.Med. 302 (23): 1283 81980)]. AL amyloidosis is caused by peculiar monoclonal immunoglobulin light chains which form amyloid fibrils. These monoclonal light chains are produced by monoclonal plasma cells with a low mitotic index which accounts for their well known insensitivity to chemotherapy. The malignancy of these cells consists in their protidosynthetic activity.

The clinical course of the disease depends on the selectivity of organ involvement; the prognosis can be extremely unfavourable in case of heart infiltration (median survival<12 months) or more benign in case of kidney involvement (median survival approx. 5 years). Considering the relative insensitivity of the amyloidogenic deposits to proteolytic digestion, a molecule that can block or slow amyloid formation and increase the solubility of existing amyloid deposits seems the only reasonable hope for patients with AL amyloidosis. Furthermore, since the supermolecular organization of the amyloid fibrilis is the same for all types of amyloid, the availability of a drug that interferes with amyloid formation and increases the solubility of existing deposits, allowing clearance by normal mechanisms, could be of great benefit for all types of amyloidosis, and in particular for the treatment of Alzheimer's disease.

Indeed, the major pathological feature of Alzheimer's Disease (AD), Downs Syndrome, Dementia pugilistic and Cerebral amyloid angiopaty is amyloid deposition in cerebral parenchima and vessel walls. These markers are associated with neuronal cell loss in cerebral cortex, limbic regions and subcortical nuclei. Several studies have shown that selective damage to various neuronal systems and synapse loss in the frontal cortex have been correlated with cognitive decline. The pathogenesis and molecular basis of neurodegenerative processes in AD is not known, but the role of β-amyloid, deposited in brain parinchema and vessel walls has been highlighted by recent report of its neurotoxic activity in vitro and in vivo (Yanker et al. Science, 245: 417, 1990. Kowall et al. PNAS, 88: 7247, 1991). Furthermore, the segregation of familiar AD with mutation of the amyloid precursor protein (APP) gene has aroused interest in the potential pathogenetic function of β-amyloid in AD [Mullan M. et al. TINS, 16(10): 392 (1993)]. The neurotoxicity of β-amyloid has been associated with the fibrilogenic properties of protein. Studies with homologous synthetic peptides indicate that hippocampal cells were insensitive to exposure to fresh β1-42 solution for 24 h while their viability decreased when neurons were exposed to Aβ1-42 previously stored in saline solution for 2–4 days at 37° C. to favour the peptide aggregation. The relationship between fibrils and neurotoxicity is further supported by recent evidence showing that the soluble form of β-amyloid is produced in vivo and in vitro during normal cellular metabolism (Hass et al. Nature, 359, 322, 1993) and only when it aggregates in congophilic formation was associated with dystrophic neurites. On the other hand, non-congophilic "preamyloid" formation of β-amyloid was not associated with neuronal alteration (Tagliavini et al. Neurosci.Lett. 93: 191, 1988). The neurotoxicity of β-amyloid has also been confirmed using a peptide homologue β-amyloid fragment 25-35 (β25-35) retaining the self-aggregating properties of the complete β-amyloid fragment β1-42.

Chronic but not acute exposure of hippocampal neurons to micromolar concentration of β25-35 induced neuronal death by the activation of a mechanism of programmed cell death known as apoptosis (Forloni et al. NeuroReport, 4: 523, 1993). Here again, neurotoxicity was associated with the self aggregating property of β25-35.

Other neurodegenerative disorders such as spongiform encephalopathy (SE) are characterized by neuronal death and extracellular deposition of amyloid, in this case originated from Prion (PrP) protein. In analogy with the observation that β-amyloid is neurotoxic, the effects of synthetic peptides homologous to different segments of PrP on the viability of primary rat hippocampal neurons have been investigated. The chronic application of peptide corresponding to PrP 106-126 induced neuronal death by apoptosis while under the same conditions all the other peptides tested and the scrambled sequence of PrP 106-126 did not reduce cell viability (Forloni et al., Nature 362: 543). PrP 106-126 resulted highly fibrillogenic in vitro and when stained with Congo red, the peptide aggregate showed green birefrangence indicative of the β-sheets conformation characteristic of amyloid.

The compounds of the present invention can be used to make medicaments useful to prevent or arrest the progression of diseases caused by amyloid proteins, such as AL amyloidosis, Alzheimer or Downs Syndrome.

The compounds of the present invention were tested for their intrinsic cytotoxicity on PC 12 cell cultures, according to the standard procedures. All of the compounds were found to be non-cytotoxic to a concentration of 10 mM.

The present invention also includes within its scope pharmaceutical compositions comprising one or more compounds of the formula (I) as active ingredients, in association with pharmaceutically acceptable carriers, excipients or other addictives, if necessary.

The pharmaceutical compositions containing a compound of formula 1 or salts thereof may be prepared in a conventional way by employing conventional non-toxic pharmaceutical carriers or diluents in a variety of dosage forms and ways of administration.

In particular, the compounds of the formula 1 can be administered:

A) orally, for example, as tablets, troches, lozenges, aqueous or oily suspensions, dispersible powders or granules, emulsions, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch or alginic acid; binding agents, for example maize starch, gelatin or acacia, and lubrificating agents, for example magnesium stearate or stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulation for oral use may also be presented as hard gelatin capsules wherein the active ingredient is mixed with an inert solid diluent, for example, calcium carbonate, calcium phosphate or kaolin, or a soft gelatin capsules wherein the active ingredient is mixed with water or an oil medium, for example, peanut oil, liquid paraffin or olive oil. Aqueous suspensions contain the active materials in admixture with excipients suitable for the manufacture of aqueous suspensions.

Such excipients are suspending agents, for example, sodium carboxymethylcellulose, methylcellulose, hydroxy, propylmethyl cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and a hexitol anhydrides, for example polyoxyethylene sorbitan monooleate. The said aqueous suspensions may also contain one or more preservatives, for example, ethyl or n-propyl p-hydroxybenzoate, one or more colouring agents, one or more flavouring agents, or one or more sweetening agents, such as sucrose or saccharin. Oily suspension may be formulated by suspending the active ingredient in a vegetable oil, for example arachis oil, olive oil, sememe oil or coconut oil or in a mineral oil such as liquid paraffin. The oily suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an autoxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and agents, may also be present.

The pharmaceutical compositions of the invention may also be in the form of oil-in-water emulsions. The oily phase may be a vegetable oil, for example olive oil or arachis oils, or a mineral oil for example liquid paraffin or mixtures of these. Suitable emulsifying agents may be naturally-occurring gums, for example gum acacia or gum tragacanth, naturally-occurring phosphatides, for example soy bean, lecithin, and esters o partial esters derived from fatty acids and hexitol anhydrides, for example sorbitan mono-oleate, and condensation products of the said partial esters with ethylene oxide, for example polyoxy ethylene sorbitan monooleate. The emulsion may also contain sweetening and flavouring agents. Syrups and elixirs may be formulated with sweetening agents, for example glycerol, sorbitol or sucrose. Such formulations may also contain a demulcent, a preservative and flavouring and colouring agents.

B) Parenterally, either subcutaneously or intravenously or intramuscularly, or intrasternally, or by infusion techniques, in the form of sterile injectable aqueous or olagenous suspension. The pharmaceutical compositions may be in the form of a sterile injectable aqueous or olagenous suspensions.

This suspension may be formulated according to the known art using those suitable dispersing of wetting agents and suspending agents which have been above. The sterile injectable preparation may also be a sterile injectable solution or suspension in a non-toxic parenterally-acceptable diluent or solvent for example, as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oils may be conventionally employed including synthetic mono- or diglycerides. In addition fatty acids such as oleic acid find use in the preparation of injectables.

The present invention also provides a method of controlling amyloidosis diseases, and/or of preventing or arresting the progression of diseases caused by amyloid proteins, which method comprises administering a therapeutically effective amount of one or more compounds of the formula 1 to a human or animal, e.g. a mammal, in need of such treatment.

Daily doses are in range of about 0.1 to about 50 mg per kg of body weight, according to the activity of the specific compound, the age, weight and conditions of the subject to be treated, the type and the severity of the disease, and the frequency and route of administration; preferably, daily dosage levels are in the range of 5 mg to 2 g. The amount of active ingredient that may be combined with the carrier materials to produce a single dosage form will vary depending upon the host treated and the particular mode of administration. For example, a formulation intended for the oral may contain from 5 mg to 2 g of active agent compounded with an appropriate and convenient amount of carrier material which may vary from about 5 to about 95 percent of the total composition. Dosage unit forms will generally contain between from about 5 mg to about 500 mg of the active ingredient.

The following Examples illustrate the invention without limiting it.

EXAMPLE 1

Preparation of 8-N-(3,4-dimethoxybenzyl)-anthrazalone (1a)

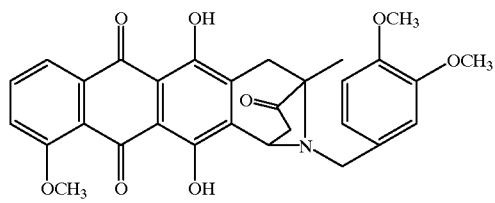

Daunorubicin (2a, 1.58g, 3mmol) was dissolved in dry pyridine (20 ml), added with 3,4-dimethoxybenzylamine (2 g, 12 mmol) and kept at room temperature for 16 hours. After that, the reaction mixture was added with aqueous 1N HCl (400 ml) and extracted with methylene chloride (200 ml). The organic phase was washed with water (2×200 ml), dried over anhydrous sodium sulphate, concentrated to small volume under reduced pressure and flash chromatographed on silica gel using a mixture of toluene acetone (9:1 by volume) as eluting system to give the title compound 1a (1 g). TLC on Kieselgel plate $F_{254}$ (Merck), eluting system methylene chloride acetone (95:5 by volume) $R_f$=0.56 FAB-MS(+): m/z 530 [MH]$^+$; 380 [M–CH$_2$(C$_6$H$_3$)(OCH$_3$)$_2$+ 2H]$^+$;

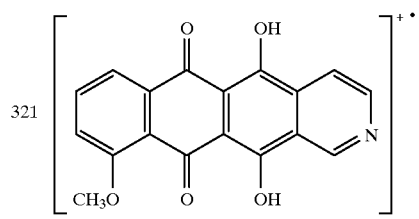

$^1$HNMR (400 MHz, CDCl$_3$) δ: 1.43 (s, 3H, C$\underline{H}_3$) ; 2.34 (d, J=17.5 Hz, 1H, C$\underline{H}$(H)-12); 2.66, 2.77 (two doublets, J=19.4 Hz, 2H, C$\underline{H}_2$-10); 2.81 (dd, J=7.3, 17.5 Hz, 1H, CH(H̲)-12); 3.24, 3.79 (two doublets, J=12.8 Hz, 2H, N-C$\underline{H}_2$-Ph); 53.85, 3.86 (2×s, 6H, 2×OC$\underline{H}_3$); 4.08 (s, 3H, 4-OC$\underline{H}_3$); 4.77 (d, J=7.3 Hz, 1H, H̲-7); 6.6–6.8 (m, 3H, aromatic hydrogens); 7.38 (d, J=7.6 Hz, 1H, H̲-3); 7.77 (dd, J=7.6, 7.8 Hz, 1H, H̲-2); 8.03 (d, J=7.8 Hz, 1H, H̲-1); 13.22 (s, 1H, O$\underline{H}$-11); 13.50 (s, 1H, O$\underline{H}$-6).

EXAMPLE 2

Preparation of Anthrazalone (1b)

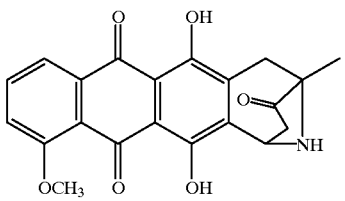

8-N-(3,4-dimethoxybenzyl)-anthrazalone (1a, 0.5 g, 1 mmol) was dissolved in a mixture of methylene chloride (20 ml) and water (1 ml) and treated with 2,3-dichloro-5,6-dicyano-1,4-benzoquinone (DDQ, 0.25 g, 1 mmol) at room temperature. After 4 hours, the reaction mixture was washed with aqueous 5% sodium hydrogen carbonate (3×100 ml) then with water. The organic phase was dried over anhydrous sodium sulphate and the solvent was removed under reduced pressure to afford the title compound 1b (0.35 g) which was converted into the corresponding hydrochloride salt derivative by treatment with methanolic anhydrous hydrogen chloride.

TLC on Kieselgel plate $F_{254}$ (Merck), eluting system methylene chloride acetone (90:10 by volume) $R_f$=0.26 FD-MS: 380 [MH]$^+$; 362 [M–NH$_3$]+.

$^1$HNMR (400 MHz, CDCl$_3$) δ: 1.45 (s, 3H, C$\underline{H}_3$); 2.43 (d, J=17.5 Hz, 1H, C$\underline{H}$(H)-12); 2.76, 2.84 (two doublets, J=19.2 Hz, 2H, C$\underline{H}_2$-10); 2.86 (dd, J=7.3, 17.5 Hz, 1H, CH(H̲)-12); 4.08 (s, 3H, OC$\underline{H}_3$); 5.14 (d, J=7.3 Hz, 1H, H̲-7); 7.37 (d, J=8.5 Hz, 1H, H̲-3); 7.76 (dd, J=7.7, 8.5 Hz, 1H, H̲-2); 8.01 (d, J=7.7 Hz, 1H, H̲-1); 13.14 (s, 1H, O$\underline{H}$-11); 13.60 (s, 1H, O$\underline{H}$-6).

EXAMPLE 3

Preparation of 8-N-(Pyridinmethyl)-anthrazalone (1c)

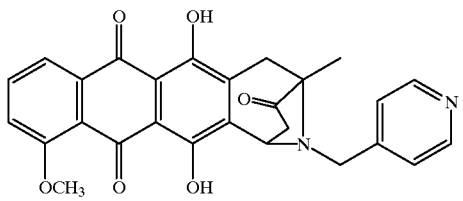

The title compound 1c was prepared from daunorubicin (2a, 1.58 g, 3 mmol) and 4-aminomethylpyridine (1.2 g, 12 mmol) following the same procedure as described in Example 1.

Yield, 0.95 g. TLC on Kieselgel plate $F_{254}$ (Merck), eluting system methylene chloride acetone (80:20 by volume) $R_f$=0.4 FAB-MS(+) : m/z 471 [MH]$^+$; 380 [M–CH$_2$(C$_5$H$_4$N)+2H]$^+$;

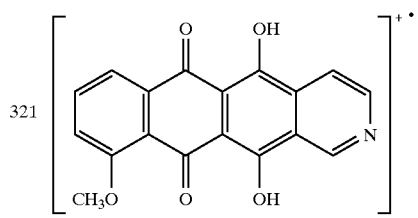

$^1$HNMR (400 MHz, CDCl$_3$) δ: 1.39 (s, 3H, C$\underline{H}_3$); 2.50 (d, J=17.9 Hz, 1H, C$\underline{H}$(H)-12); 2.78 (s, 2H, C$\underline{H}_2$-10); 2.96 (dd, J=7.3, 17.9 Hz, 1H, CH($\underline{H}$)-12); 3.70, 4.07 (two doublets, J=16.7 Hz, 2H, N$^+$—C$\underline{H}_2$-Pyrid.); 4.07 (s, 3H, OC$\underline{H}_3$); 4.76 (d, J=7.3 Hz, 1H, $\underline{H}$-7) ; 7.40 (d, J=7.3 Hz, 1H, $\underline{H}$-3) ; 7.79 (dd, J=7.3 Hz, 1H, $\underline{H}$-2); 7.89 (d, J=6.0 Hz, 2H, Pyridine hydrogens); 8.02 (d, J=7.7 Hz, 1H, $\underline{H}$-1); 8.70 (d, J=6.0 Hz, 2H, Pyridine hydrogens) ; 13.14 (s, 1H, O$\underline{H}$-11); 13.45 (s, 1H, O$\underline{H}$-6).

EXAMPLE 4

Preparation of 4-demethoxy-8-N-(pyridinmethyl)-anthrazalone (1d)

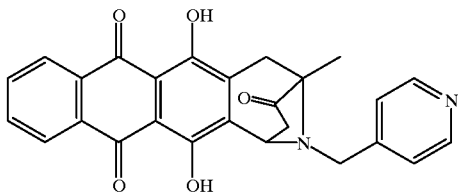

The title compound id was prepared from 4-demethoxydaunorubicin (23, 1.38 g, 3 mmol) and 4-aminomethylpyridine (1.2 g, 12 mmol) following the same procedure as described in Example 1.

Yield, 0.87 g. TLC on Kieselgel plate $F_{254}$ (Merck), eluting system methylene chloride acetone (80:20 by volume) $R_f$=0.46 FAB-MS(+) : m/z 441 [MH]$^+$; 350 [M–CH$_2$(C$_5$H$_4$N)+2H]$^+$;

$^1$HNMR (200 MHz, CDCl$_3$) δ: 1.41 (s, 3H, C$\underline{H}_3$); 2.46 (d, J=17.6 Hz, 1H, C$\underline{H}$(H)-12); 2.73 (m, 2H, C$\underline{H}_2$-10); 2.89 (dd, J=7.0, 17.6 Hz, 1H, CH($\underline{H}$)-12); 3.37, 3.85 (two doublets, J=14.6 Hz, 2H, N-C$\underline{H}_2$-Pyrid.); 2.73 (d, J=7.0 Hz, 1H, H-7); 7.24 (m, 2H, Pyridine hydrogens), 7.80 (m, 2H, $\underline{H}$-2+H-3); 8.28 (m, 2H, $\underline{H}$-1+$\underline{H}$-4); 8.54 (2H, Pyridine hydrogens); 13.05, 13.16 (2xs, 2H, O$\underline{H}$-6+O$\underline{H}$-11).

EXAMPLE 5

Preparation of 8-N-benzyl-anthrazalone (1e)

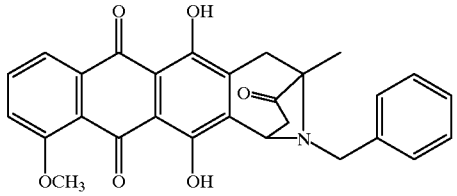

The title compound 1e was prepared from daunorubicin (2a, 1.58 g, 3 mmol) and benzylamine (1.2 g, 12 mmol) following the same procedure as described in Example 1.

Yield, 1 g. TLC on Kieselgel plate $F_{254}$ (Merck), eluting system methylene chloride acetone (90:10 by volume) $R_f$=0.7 FAB-MS (+) : m/z 470 [MH]$^+$; 320 [M–CH$_2$(C$_6$H$_5$)+2H]$^+$;

$^1$HNMR (200 MHz, CDCl$_3$) δ: 1.42 (s, 3H, C$\underline{H}_3$); 2.37 (d, J=17.4 Hz, 1H, C$\underline{H}$(H)-12); 2.68, 2.76 (two doublets, J=19.6 Hz, 2H, C$\underline{H}_2$-10); 2.81 (dd, J=7.0, 17.4 Hz, 1H, CH($\underline{H}$)-12); 3.30, 3.84 (two doublets, J=13.2 Hz, 2H, N-C$\underline{H}_2$-Ph); 4.07 (s, 3H, 4-OC$\underline{H}_3$); 4.74 (d, J=7.0 Hz, 1H, $\underline{H}$-7); 7.2–7.3 (m, 5H, Phenyl hydrogens); 7.38 (dd, J=1.0, 8.4 Hz, 1H, $\underline{H}$-3); 7.77 (dd, J=7.7, 8.4 Hz, 1H, $\underline{H}$-2); 8.02 (dd, J=1.0, 7.7 Hz, 1H, $\underline{H}$-1); 13.22, 13.42 (2xs, 2H, O$\underline{H}$-6+O$\underline{H}$-11).

EXAMPLE 6

Preparation of 4-demethoxy-8-N-benzyl-anthrazalone (1f)

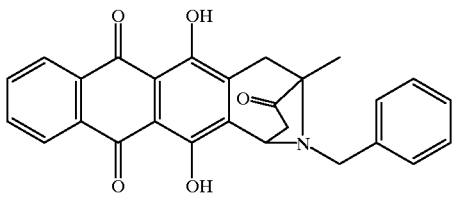

The title compound if was prepared from 4-demethoxy-daunorubicin (2c, 1.38 g, 3 mmol) and benzylamine (1.2 g, 12 mmol) following the same procedure as described in Example 1.

Yield, 0.9 g. TLC on Kieselgel plate $F_{254}$ (Merck), eluting system methylene chloride acetone (80:20 by volume) $R_f$=0.84 FAB-MS (+): m/z 440 [MH]$^+$; 290 [M–CH$_2$(C$_6$H$_5$)+2H]$^+$;

$^1$HNMR (200 MHz, CDCl$_3$) δ: 1.44 (s, 3H, C$\underline{H}_3$) ; 2.38 (d, J=17.4 Hz, 1H, C$\underline{H}$(H)-12); 2.70, 2.78 (two dublets, J=19.7 Hz, 2H, C$\underline{H}_2$-10); 2.85 (dd, 7.2, 17.4 Hz, 1H, CH($\underline{H}$)-12); 3.31, 3.87 (two doublets, J=13.0 Hz, 2H, N-C$\underline{H}_2$-Ph); 4.74 (d, J=7.2 Hz, 1H, $\underline{H}$-7); 7.2–7.3 (m, 5H, Phenyl hdrogens); 7.83 (m, 2H, $\underline{H}$-2+$\underline{H}$-3); 8.33 (m, 2H, $\underline{H}$-1+$\underline{H}$-4); 13.1, 13.2 (2xs, 2H, O$\underline{H}$-6+O$\underline{H}$-11).

EXAMPLE 7

Preparation of 4-demethoxy-8-N-(3,4-dimethoxybenzyl)-anthrazalone (1g)

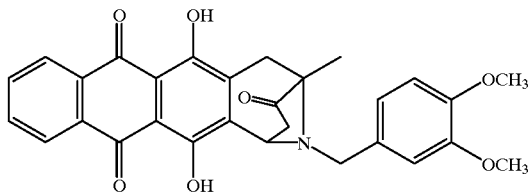

The title compound 1g was prepared by reacting 4-demethoxy-daunorubicin (2c, 1.38 g, 3 mmol) and 3,4-dimethoxybenzylamine (2 g, 12 mmol) as described in Example 1. Yields 1 g.

TLC on Kieselgel plate $F_{254}$ (Merck), eluting system methylene chloride acetone (95:5 by volume) $R_f$=0.65 FAB-MS(+) m/z 500 [MH]$^+$; 350 [M–CH$_2$(C$_6$H$_3$) (OCH$_3$)$_2$+ 2H]$^+$;

EXAMPLE 8

Preparation of 4-demethoxy-anthrazalone (1h)

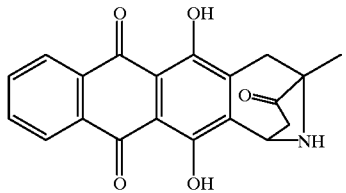

4-demethoxy-8-N-(3,4-dimethoxybenzyl)-anthrazalone (1 g, 0.5 g, 1 mmol) was transformed into the title compound 1h in presence of DDQ as described in Example 2. Yield 0.4 g.

TLC on Kieselgel plate $F_{254}$ (Merck), eluting system methylene chloride acetone (95:5 by volume) $R_f$=0.34 FD-MS: 350 [MH]$^+$ $^1$HNMR (200 MHz, CDCl$_3$) δ: 1.46 (s, 3H, C$\underline{H}$$_3$); 2.45 (, J=17.7 Hz, 1H, C$\underline{H}$(H)-12); 2.81, 2.86 (two doublets, J=19.4 Hz, 2H, C$\underline{H}$$_2$-10); 2.87 (dd, J=7.0, 17.7 Hz, 1H, CH($\underline{H}$)-12); 5.14 (d, J=7.0 Hz, 1H, $\underline{H}$-7); 7.83 (m, 2H, $\underline{H}$-2+$\underline{H}$-3); 8.33 (m, 2H, $\underline{H}$-1+$\underline{H}$-4); 13.18, 13.25 (2×s, 2H, O$\underline{H}$-6+O$\underline{H}$-11).

EXAMPLE 9

Preparation of 8-N-allyl-anthrazalone (1i)

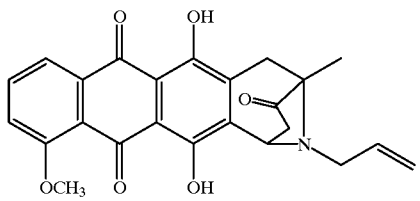

The title compound 1i was prepared by reacting daunorubicin (2a, 1.58 g, 3 mmol) with allylamine (0.9 g, 12 mmol) as described in Example 1. The crude material was flash chromatographed on silica gel by using a mixture of methylene chloride and acetone (98:2 by volume) as eluting system to give pure 1i (0.85 g).

TLC on Kieselgel plate $F_{254}$ (Merck), eluting system methylene chloride $R_f$=0.1

$^1$HNMR (200 MHz, CDCl$_3$) δ: 1.37 (s, 3H, C$\underline{H}$$_3$); 2.41 (d, J=17.6 Hz, 1H, C$\underline{H}$(H)-12); 2.64 (m, 2H, C$\underline{H}$$_2$-10); 2.88 (dd, J=7.2, 17.6 Hz, 1H, CH($\underline{H}$)-12);2.8–3.4 (m, 2H, C$\underline{H}$$_2$CH=CH$_2$); 4.04 (s, 3H, 4-OC$\underline{H}$$_3$); 5.0–5.2 (m, 2H, CH$_2$CH=C$\underline{H}$$_2$); 5.90 (m, 1H, CH$_2$C$\underline{H}$=CH$_2$); 7.37 (d, J=8.4 Hz, 1H, $\underline{H}$-3); 7.75 (dd, J=7.6, 8.4 Hz, 1H, $\underline{H}$-2); 8.00 (d, J=7.6 Hz, 1H, $\underline{H}$-1); 13.0, 13.5 (2×s, 2H, O$\underline{H}$-6+O$\underline{H}$-11).

EXAMPLE 10

Preparation of 8-N-benzyl-13-dihydro-anthrazalone (1j)

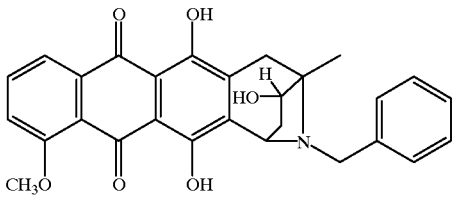

8-N-benzylanthrazalone (1e, 0.75 g, 1.5 mmol), prepared as described in Example 5, was dissolved in anhydrous methylene chloride (209 ml) and treated with tetrabutylammonium borohydride (1.6 g) at room temperature for 5 minutes. After that, the reaction mixture was poured in aqueous 1N hydrochloric acid and extracted with methylene chloride. The organic phase was separated, washed with water and dried over anhydrous sodium sulphate. The solvent was removed under reduced pressure and the crude material was flash chromatographed on silica gel using a mixture of toluene and acetone (9:1 by volume) as eluting system to give the title compound 1j (0.65 g).

TLC on Kieselgel plate $F_{254}$ (Merck), eluting system methylene chloride acetone (90:10 by volume) $R_f$=0.4

$^1$HNMR (200 MHz, CDCl$_3$) δ: 1.42 (s, 3H, C$\underline{H}$$_3$); 1.51 (m, 1H, CH($\underline{H}$)-12); 2.6 (m, 2H, C$\underline{H}$(H)-12+C$\underline{H}$(H)-10); 3.06 (d, J=19.6 Hz, 1H, CH($\underline{H}$)-10); 3.21, 3.79 (two doublets, J=12.9 Hz, 2H, N-C$\underline{H}$$_2$-PH); 4.08 (s, 3H, OC$\underline{H}$$_3$); 4.20 (m, 1H, $\underline{H}$-9); 4.34 (d, J=7.2 Hz, 1H, $\underline{H}$-7); 7.1–7.3 (m, 5H, Phenyl hydrogens); 7.37 (dd, J=1.0, 8.8 Hz, 1H, $\underline{H}$-3); 7.76 (dd, J=7.7, 8.8 Hz, 1H, $\underline{H}$-2); 8.02 (dd, J=1.0, 7.7 Hz, 1H, $\underline{H}$-1); 13.24, 13.51 (2×s, 2H, O$\underline{H}$-6, O$\underline{H}$-11).

EXAMPLE 11

Preparation of 8-N-(3,4-dimethoxybenzyl)-13-dihydro-anthrazalone (1k)

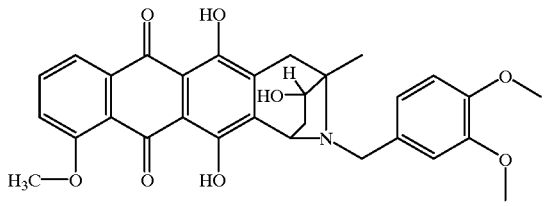

8-N-(3,4-dimethoxybenzyl)anthrazalone (500 mg, 1.1 mmol) was dissolved under argon in THF (20 ml) and MgBr$_2$.OEt$_2$ (1.13 g, 4.4 mmol) was added under stirring. The mixture was cooled at −50 ° C. and NaBH$_4$ (84 mg, 2.2 mmol) added in small portions during 10 minutes. Methanol (2 ml) was added and the reaction mixture was stirred for an additional hour. Acetone (2 ml) was added and the mixture was poured into a cooled water solution of oxalic acid (100 mg in 100 ml of water) and extracted with methylene chloride. The organic phase was separated, washed with water and dried over anhydrous sodium sulphate. The solvent was removed under reduced pressure and the crude material was flash chromatographed on silica gel using a mixture of methylene chloride, methanol, acetic acid (30:2:1 by volume) as eluting system to give 320 mg of a single isomer product. TLC: Kieselgel plate F254 (Merck), eluting system methylene chloride, methanol, acetic acid (30:2:1 by volume), R$_f$=0.5.

FAB-MS: m/z 532 [M+H]$^+$; m/z 382 [M+2H−CH$_2$C$_6$H$_3$(OCH$_3$)$_2$]$^+$.

$^1$H-NMR (600 MHz, DMSO-d$_6$) d: 1.57 (m, 1H, H-8); 1.70 (s, 3H, CH$_3$); 2.74 (m, 1H, H-8) 2.98 (d, 1H, J=19.0 Hz, H-10); 3.40 (d, 1H, J=19.0 Hz, H-10); 3.64 (s, 3H, OCH$_3$); 3.74 (s, 3H, OCH$_3$); 3.84 (m, 1H, CH(H)-Ph); 3.99 (s, 3H, OCH$_3$); 4.33 (m, 1H, H-9); 4.42 (m, 1H, CH(H)-Ph); 4.53 (m, 1H, H-7); 5.95 (s, 1H, OH-9); 6.77 (m, 1H, aromatic hydrogen); 6.92 (m, 1H, aromatic hydrogen); 6.94 (m, 1H, aromatic hydrogen); 7.69 (m, 1H, aromatic hydrogen); 7.94 (m, 2H, aromatic hydrogens); 11.09 (broad signal, 1H, NH$^+$), 13.03 (s, 1H, OH), 13.56 (s, 1H, OH).

EXAMPLE 12

Preparation of 8-N-(pyridinmethyl)-13-anthrazalone oxime(1l)

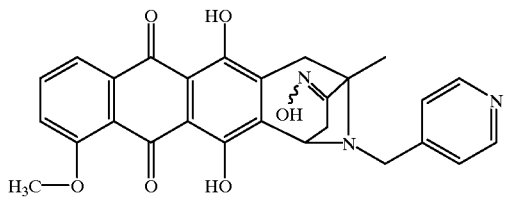

8-N-(pyridinmethyl)-13-anthrazalone (1c, 210 mg, 0.5 mmol) was dissolved in EtOH (10 ml) and treated with hydroxylamine hydrochloride (59.5 mg, 0.85 mmol) and sodium acetate trihydrate (66 mg, 0.5 mmol) dissolved in 0.25 ml of water. The reaction mixture was refluxed for two hours under stirring, poured into water and extracted with methylene chloride. The organic phase was separated, washed with water and dried over anhydrous sodium sulphate.

The solvent was removed under reduced pressure and the crude material was flash chromatographed on silica gel using a mixture of methylene chloride and acetone (8:2 by volume) as eluting system to give 120 mg of the mixture of the oximes. TLC: Kieselgel plate F254 (Merck), eluting system methylene chloride and acetone (8:2 by volume), R$_f$=0.44 and 0.36.

FAB-MS: m/z 486 [M+H]$^+$; m/z 470 [M+H−O]$^+$; m/z 468 [M+H−H$_2$O]$^+$.

$^1$H-NMR (400 MHz, DMSO-d$_6$) d: 1.40 (s, 3H, CH$_3$); 2.52 (d, 1H, J=17.2 Hz, H-8a); 2.57 (d, 1H, J=18.8 Hz, H-10); 2.89 (dd, 1H, J=17.2 and 6.8 Hz, H-8b); 2.97 (d, 1H, J=18.8 Hz, H-10); 3.63 (d, 1H, J=18.0 Hz, CH(H)-Ph); 3.96 (s, 3H, OCH$_3$); 4.22 (d, 1H, J=18.0 Hz, CH(H)-Ph); 4.52 (d, 1H, J=6.8 Hz, H-7); 7.65 (dd, 1H, J=6.8 and 2.9 Hz, H-3); 7.91 (m, 2H, H-1+H-2); 7.95 (m, 2H, H-3'+H-5'); 8.78 (m, 2H, H-2'+H-6'); 10.77 (s, 1H, =N-OH), 13.09 (s, 1H, OH), 13.53 (s, 1H, OH).

Biological test

Anthrazalinone derivatives of formula 1 interfere with the self-aggregating activity of β-amyloid fragment 25-35 and PrP fragment 106-126 by using light scattering analysis. β25-35 (GSNKGAIIGLH) and PrP 106-126 (KTNMKHMAGAAAAGAVVGGLG) were synthesized using solid phase chemistry by a 430A Applied Biosystems Instruments and purified by reverse-phase HPLC (Beckman Inst. mod 243) according to Forloni et al., Nature 362: 543, 1993.

Light scattering of the peptide solutions was evaluated by spectrofluorimetriy (Perkin Elmer LS 50B), excitation and emission were monitored at 600 nm. β-amyloid fragment 25-35 and PrP 106-126 were dissolved at a concentration of 0.5 to 1 mg/ml (0.4–0.8 mM and 0.2–0.4 mM respectively) in a solution of phosphate buffer pH 5, 10 mM spontaneously aggregate within an hour.

8-N-pyridinmethylen-anthrazalone (1c), dissolved at several concentration (0.2–2 mM) in Tris buffer 5 mM pH 7.4, was added to the peptidic solutions at the moment of their preparation in order to evaluate the process of fibrillogenesis. Compound 1c, added at equimolar concentration with β-amyloid fragment 25-35 and PrP 106-126, showed complete prevention of the agregation.

Thioflavin T assay

Stock solutions of A β25-35 peptide were prepared by dissolving the lyophilized peptide in dimethyl sulfoxide (DMSO) at a concentration of 7.07 mg/ml.

Aliquotes of this solution were dissolved in 50 mM phosphate buffer pH 5 so as to obtain a final peptide concentration of 100 mM and incubated for 24 hours at 25° C. with or without 30 mM test compound in a final volume of 113 ml. The compounds were previously dissolved in DMSO at a concentration of 3.39 mM; the final DMSO percentage (v/v) in the incubation mixtures was less than 3%.

Fluorescence measurements were carried out as described by Naiki et al., Anal. Biochem. 177, 244, 1989 and by H. LeVine III, Protein Sci. 2, 404, 1993. Briefly, the incubated samples were diluted at a peptide concentrartion of 8 mg/ml in 50 mM sodium citrate buffer pH 5 containing 47 mM thioflavin T (ThT) in a final volume of 1.5 ml. Fluorescence was measured with excitation at 420 nm and emission at 490 nm in a Kontron fluorescence spectrophotometer and the values were averaged after subtracting the background fluorescence of 47 mM ThT. The results are expressed as relative fluorescence, i.e. the percentage of the fluorescence of the A β25-35 peptide incubated alone (control). Table 1 reports the results of some of the compounds.

TABLE 1

| COMPOUND | RELATIVE FLUORESCENCE |
|---|---|
| 1b | 40.26 |
| 1c | 6.82 |
| 1k | 15.70 |
| 1l | 1.99 |

We claim:

1. A compound of formula I

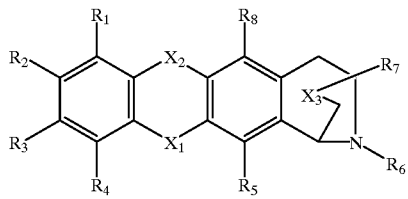

wherein:

$X_1$ and $X_2$ are independently selected from C=O, C=NH and $CH_2$;

$X_3$ is selected from $CH_2$, C=O, CHOH,

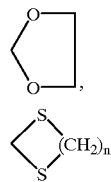

wherein n=2 or 3, and

C=N($R_9$) wherein $R_9$ is hydroxy or amino-aryl;

$R_1$, $R_2$, $R_3$ and $R_4$ are independently selected from hydrogen, hydroxyl, $C_{1-16}$ alkyl, $C_{1-16}$ alkoxyl, $C_{3-8}$ cycloalkoxyl, halogen, amino which may be unsubstituted or mono- or di-substituted by acyl, trifluoroacyl, aralkyl or aryl groups, and $OSO_2(R_{10})$ wherein $R_{10}$ is alkyl or aryl;

$R_5$ and $R_8$ are independently selected from hydrogen, hydroxyl, $C_{1-16}$ alkoxyl, halogen, amino which may be unsubstituted or mono- or di-substituted by acyl, trifluoroacyl, aralkyl or aryl groups, and $OSO_2(R_{10})$ wherein $R_{10}$ is as above defined;

$R_6$ is selected from the group consisting of hydrogen, $R_B$—$CH_2$— (wherein $R_B$ is an aryl or heterocyclyl group), a group of formula $R_C$—CH=CH—, (wherein Rc is hydrogen or $C_{1-5}$ alkyl), $C_{1-16}$ alkyl, $C_{2-8}$ alkenyl, $C_{3-8}$ cycloalkyl, acyl of formula —C($R_{11}$)=O (wherein $R_{11}$ is selected from hydrogen, $C_{1-16}$ alkyl, $C_{3-8}$ cycloalkyl, hydroxyalkyl, heterocyclyl, aryl araloxyalkyl, and acyloxyalkyl) and an acyl residue of a naturally occurring or a synthetic amino acid or di- or tri-peptide;

$R_7$ is selected from the group consisting of hydrogen, methyl, $CH_2OH$, $CH_2O$—$R_{12}$ (wherein $R_{12}$ is the group tetrahydropyranyl (THP), or a saccharide of the formula

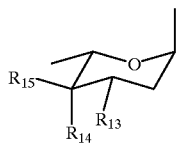

in which $R_{13}$ is amino or aminoacyl, $R_{14}$ and $R_{15}$ are both hydrogen or one of $R_{14}$ and $R_{15}$ is hydrogen and the other of $R_{14}$ and $R_{15}$ is hydroxy or alkoxy or halogen or a group $OSO_2(R_{10})$ as defined above), $CH_2$—O—Ph—(amino) (wherein the amino may be unsubstituted or mono- or di-substituted by alkyl, acyl, trifluoroacyl, aralkyl or aryl) and $CH_2$-amino (wherein the amino is mono- or di-substituted by an alkyl, acyl, trifluoroacyl, aralkyl or aryl group or the amino is within an heterocyclic ring optionally substituted with $C_{1-16}$ alkyl or $C_{1-16}$ alkyloxy or aryloxy), or a pharmaceutically acceptable salt thereof.

2. A compound according to claim 1, in which $X_1$ and $X_2$ are independently selected from C=O and C=NH;

$X_3$ is selected from $CH_2$; C=O, CHOH and C=N($R_9$) wherein $R_9$ is hydroxy or amino-aryl;

$R_1$, $R_2$, $R_3$ and $R_4$ are independently selected from hydrogen, hydroxyl, $C_{1-4}$ alkoxyl, $C_{3-8}$ cycloalkoxyl, O-mesyl (O—$SO_3CH_3$), amino and amino-benzyl;

$R_5$ and $R_8$ are independently selected from hydrogen, hydroxyl, $C_1$–$C_4$ alkoxyl, halogen, amine, amino-benzyl; and amino-trifluoroacetyl;

$R_6$ is selected from hydrogen $R_B$—$CH_2$, wherein $R_B$ is as defined in claim 1, $C_{1-10}$ alkyl, $C_{2-6}$ alkenyl, acyl of formula —C($R_{11}$)=O (where in $R_{11}$ is selected from the group consisting of $C_{1-10}$ alkyl, hydroxylalkyl, heterocyclyl, aryl araloxyalkyl, and acyloxyalkyl) and an acyl residue of a naturally occurring or synthetic amino acid or di- or tri-peptide; and $R_7$ is selected from the group consisting of hydrogen, methyl, $CH_2OH$, $CH_2O$—$R_{12}$ (wherein $R_{12}$ is the group tetrahydropyranyl (THP), or a saccharide of the formula

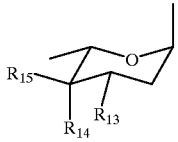

in which $R_{13}$ is amino or aminotrifluoroacetyl or amino-acetyl, $R_{15}$ is hydrogen and $R_{14}$ is hydroxy, iodine, O-mesyl, or $CH_2$—O—Ph—NH—COR wherein R is alkyl, aralkyl or aryl), and $CH_2$-amino (wherein the amino is within an heterocyclic ring optionally substituted with $C_{1-10}$ alkyl or $C_{1-5}$ alkyloxy or aryloxy); or a pharmaceutically acceptable salt thereof.

3. A compound according to claim 1, in which:

$X_1$ and $X_2$ are independently selected from C=O and C=NH;

$X_3$ is selected from $CH_2$, C=O and CHOH, $R_1$, $R_2$, $R_3$ and $R_4$ are independently selected from hydrogen, hydroxyl, methyl, methoxy, O-mesylate, amino, amino-benzyl, fluorine and chlorine;

$R_5$ and $R_8$ are independently selected from hydrogen, hydroxyl, methoxy, ethoxy, amino and amino-trifluoroacetyl;

$R_6$ is selected from hydrogen, benzyl, allyl, 3,4-dimethoxybenzyl, pyridinemethyl, (N-methyl-dihydropyridine)-methyl, nicotyl, glycyl and isoleucyl; and $R_7$ is selected from the group consisting of hydrogen, methyl, $CH_2OH$, $CH_2O$—$R_{12}$ (wherein $R_{12}$ is the group tetrahydropyranyl (THP), or a saccharide of the formula

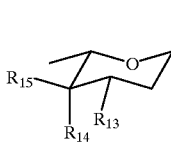

in which $R_{13}$ is amino or aminotrifluoroacetyl or aminoacetyl, $R_{15}$ is hydrogen and $R_{14}$ is iodine), and $CH_2$-amino wherein the amino is within a morpholino ring;

or a pharmaceutically acceptable salt thereof.

4. A compound according to claim 1, in which $X_1$ and $X_2$ are both C=O;

$X_3$ is C=O;

$R_1$, $R_2$ and $R_3$ are each hydrogen and $R_4$ is hydrogen, hydroxy or methoxy;

$R_5$ and $R_8$ are independently selected from hydrogen, hydroxyl, methoxy and amino;

$R_6$ is selected from hydrogen, pyridinemethyl, (N-methyl-dihydropyridine)-methyl, nicotyl, glycyl and isoleucyl; and $R_7$ is methyl;

or a pharmaceutically acceptable salt thereof.

5. A process for producing a compound of formula I, as defined in claim 1, which process comprises:

(a) reacting a compound of formula 2:

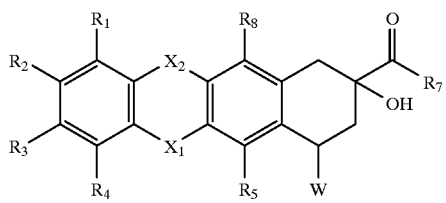

wherein $X_1$, $X_2$ and $R_1$ to $R_7$ are as defined in claim 1, and W represents a leaving group, with an amine of the formula

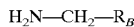

wherein $R_B$ is as defined in claim 1, to give a compound of formula I wherein $R_6$ is $R_B$—$CH_2$—;

(b) if desired, converting the thus obtained compound of formula (I) into another compound of formula (I); and/or (C) if desired, converting the compound of formula (I) to a pharmaceutically acceptable salt thereof.

6. A process according to claim 5, wherein step (a) is carried out with a 1 to 10 fold excess of amine, in an organic solvent therefor, in the presence of an organic base for from 6 to 48 hours, at from −10° C. to room temperature.

7. A process according to claim 5 wherein, in step (b), the compound of formula (I) wherein $R_6$ is $R_B$—$CH_2$— is converted to a compound of the formula I in which $R_6$ is hydrogen.

8. A process according to claim 7, wherein $R_B$ is a 3,4-dimethoxyphenyl or vinyl group and the conversion is carried out by oxidation.

9. A process according to claim 8, wherein $R_B$ is a 3,4-dimethoxyphenyl group and the oxidation is conducted using 2,3 dichloro-5,6 dicyano 1,4-benzoquinone.

10. A process according to claim 7, which further comprises converting the compound of formula (I) in which $R_6$ is hydrogen into a compound of formula I wherein $R_6$ is $C_{1-16}$ alkyl, $C_{2-8}$ alkenyl, $C_{3-8}$ cycloalkyl, an acyl group of formula —$C(R_{11})$=O, wherein $R_{11}$ is as defined above, or an acyl residue of an amino acid or of a di-or tri-tripeptide.

11. A process according to claim 5, wherein step (b) comprises the reduction of a compound of formula (I) wherein $X_3$ is C=O to give a compound of formula I wherein $X_3$ is CHOH or $CH_2$.

12. A pharmaceutical composition which comprises, as active ingredient, a compound of formula 1 as defined in claim 1, or a pharmaceutically acceptable salt thereof, in admixture with a pharmaceutically acceptable carrier or diluent.

13. A method of treating amyloidosis, comprising administering to a patient in need thereof an effective amount of a compound of formula 1 as defined in claim 1 or a pharmaceutically acceptable salt thereof.

* * * * *